United States Patent [19]

Colvin et al.

[11] Patent Number: 4,853,478

[45] Date of Patent: Aug. 1, 1989

[54] FUNCTIONALIZED MONOMERS FROM 1-(1-ISOCYANATO-1-METHLETHYL)-3 OR 4-(1-METHYLETHENYL) BENZENE

[75] Inventors: Howard A. Colvin; Kirkwood S. Cottman, both of Akron; Dane K. Parker, Massillon, all of Ohio

[73] Assignee: The Goodyear Tire & Rubber Company, Akron, Ohio

[21] Appl. No.: 16,148

[22] Filed: Feb. 18, 1987

Related U.S. Application Data

[62] Division of Ser. No. 806,688, Dec. 16, 1985, Pat. No. 4,714,772, which is a division of Ser. No. 737,742, May 28, 1985, Pat. No. 4,604,439.

[51] Int. Cl.[4] ............................................. C07D 125/06
[52] U.S. Cl. ..................................... 560/32; 558/240; 526/288; 526/301; 526/302; 526/305; 526/313; 525/32.2; 546/222
[58] Field of Search ........................................ 560/32

[56] References Cited

U.S. PATENT DOCUMENTS 4,604,439  8/1986  Colvin et al. .................. 558/240
4,714,772  12/1987  Colvin et al. .................. 558/240

*Primary Examiner*—Robert T. Bond
*Attorney, Agent, or Firm*—Bruce J. Hendricks; D. O. Nickey

[57] ABSTRACT

This invention is directed to the preparation of polymerizable monomers that are prepared from 1-(1-isocyanato-1-methylethyl)-3-(1-methylethenyl) benzene (m-TMI) and 1-(1-isocyanato-1-methylethyl)-4-(1-methylethenyl) benzene (p-TMI). The monomers prepared from m- and p-TMI can contain numerous chemical moieties, and when polymerized, produce polymers that have chemically bonded to the polymeric backbone the functional moiety. More specifically, these TMI derived monomers may contain chain breaking antioxidant moieties, peroxide decomposing antioxidant moieties, ultraviolet stabilizing moieties, triplet quenching moieties, and other chemical moieties that are useful in polymers.

3 Claims, No Drawings

4,853,478

FUNCTIONALIZED MONOMERS FROM 1-(1-ISOCYANATO-1-METHLETHYL)-3 OR 4-(1-METHYLETHENYL) BENZENE

This is a divisional of application Ser. No. 806,688 filed on Dec. 16, 1985, which issued on Dec. 22, 1987 as U.S. Pat. No. 4,714,772, which is a divisional application of Ser. No. 737,742, filed on May 28, 1985, which issued Aug. 5, 1986 as U.S. Pat. No. 4,604,439.

TECHNICAL FIELD

This invention relates to the preparation of functionalized polymerizable monomers prepared from 1-(1-isocyanato-1-methylethyl)-3-(1-methylethenyl) benzene (hereinafter m-TMI) and 1-(1-isocyanato-1-methlethyl)-4-(1-methylethenyl) benzene (hereinafter p-TMI). These monomers may contain many different chemical moieties that are desirable and useful in polymers.

BACKGROUND ART

U.S. Pat. No. 4,486,582 disclosed the preparation of reactive monomers by reacting: (1) an aromatic compound containing a polymerizable ethylenically unsaturated group and a group containing a hydrogen atom reactive with an NCO or an NCS group; (2) a compound having at least one oxyalkylene group and at least one group containing at least one hydrogen atom which is reactive with an NCO or an NCS group; and (3) a compound having an average of more than one NCO and/or NCS groups per molecule. These reactive monomers are useful as reactive modifiers for polyester and vinyl ester resins.

U.S. Pat. No. 4,429,096 discloses meta- or paraisopropenyl-α,α-dimethylbenzyl isocyanate (also known as m- or p-TMI) reacted with either an amino alcohol or a dialkylaminoethyleneamine and quaternizing the reaction product with an alkylating agent. The compound may be polymerized with a comonomer such as acrylamide to yield water soluble cationic polymers for use in water clarification, flocculation and hair spray applications.

U.S. Pat. No. 3,290,350 discloses a process for making isocyanates which comprises reacting isocyanic acid with a vinylidene compound such as diisopropenylbenzene to yield the mono and di isocyanate derivatives. U.S. Pat. No. 3,290,350 is herein incorporated by reference.

U.S. Pat. No. 3,598,866 discloses that vinyl isocyanate and isopropenyl isocyanate react with Bisphenol A, halogenated Bisphenol A, and the alkylene oxide addition products thereof to form the corresponding bis(N-alkenylcarbamate) esters. These divinyl compounds are useful monomers and crosslinking agents.

DISCLOSURE OF THE INVENTION

There are disclosed compositions of matter that are polymerizable monomers which are prepared by reacting m- or p-TMI with a compound that contains a Zerewitinoff active hydrogen atom and a chemical functionality desirable in polymers.

There is also disclosed the emulsion polymerization of functionalized monomers with at least one ethylenically unsaturated monomer or at least one diene monomer.

It has been discovered that m-TMI of the structural formula:

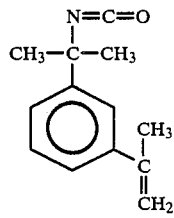

or p-TMI of the structural formula:

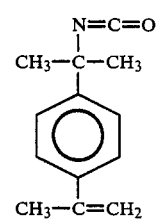

can be reacted with compounds that contain a Zerewitinoff active hydrogen atom to yield polymerizable antidegradant monomers. m-TMI or p-TMI are starting materials for the monomers of the present invention and are available from American Cyanamid.

Isocyanates, specifically m-TMI and p-TMI, react with chemical compounds or reagents which contain a reactive hydrogen, as determined by the Zerewitinoff method (J.Am.Chem.Soc., 49,3181 (1927)). Hereinafter, Zerewitinoff active hydrogens will be referred to as "active hydrogen." Active hydrogen is present in water, amines, aliphatic alcohols, phenols, acids and thiols, i.e. compounds having hydrogen attached to nitrogen, oxygen or sulfur.

m- or p-TMI, according to this invention, react with compounds containing Zerewitinoff active hydrogen to yield a variety of useful polymerizable antidegradant monomers. The antidegradant monomers of this invention can be polymerized with at least one other monomer to form polymers that have covalently bonded antidegradant functionalities pendant to the polymeric backbone.

Representative of the compounds that contain active hydrogen are the phenolic antioxidants having the general formula:

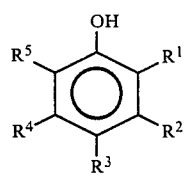

wherein $R^1$ is hydrogen or an alkyl radical having 1 to 4 carbon atoms, a cycloalkyl radical having 5 to 12 carbon atoms, or an aralkyl radical having 7 to 12 carbon atoms. $R^2$ and $R^5$ are hydrogen, $R^3$ and $R^4$ are alkyl radicals having 1 to 12 carbon atoms, cycloalkyl radicals having 5 to 12 carbon atoms, or aralkyl radicals having 7 to 12 carbon atoms or hydrogen; or polyphenolics of the formula:

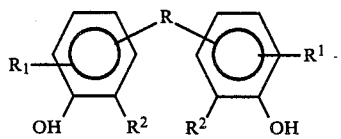

wherein R is an alkylidine radical having 1 to 4 carbon atoms, the group —O—, or the group —S—, and wherein $R^1$ is hydrogen and $R^2$ is an alkyl radical having 1 to 4 carbon atoms, cycloalkyl radicals having 5 to 12 carbon atoms, or aralkyl radicals having 7 to 12 carbon atoms. Preferably $R^2$ is a tertiary alkyl radical having 4 carbon atoms and is in a position ortho to the hydroxyl group.

Specific phenolic antioxidants having an active hydrogen atom, applicable in the present invention include:

2,2'-methylene-bis-(4-methyl-6-tert.-butylphenol)
2,2'-thio-bis-(4-methyl-6-tert.-butylphenol)
4,4'-thio-bis-(3-methyl-6-tert.-butylphenol)
4,4'-butylidene-bis-(6-tert.-butyl-3-methylphenol)
Styrenated phenol
Butylated Octylated Phenol
Butylated α-methylstyrenated phenol
Styrenated butylated m, p-cresol
2,5-diamylhydroquinone
Butylated reaction product of p-cresol and dicyclopentadiene Typical of the amine antioxidants with an active hydrogen atom that are useful in the present invention are the naphthylamines, diphenylamine derivatives, quinolines, para-phenylenediamines and the blended amines. The quinoline antidegradants are of two types--the polymerized and the substituted dihydroquinolines. Numerous para-phenylenediamines have been produced and used as antiozonants. Representative examples are Wingstay TM 300 (The Goodyear Tire & Rubber Company), Flexzone TM 3C and 6H (products of Uniroyal, Inc.) and p-aminodiphenylamine.

The monomers of this invention which have a carbon-carbon double bond and the desired chemical functionality can be polymerized by conventional methods using known addition polymerization initiators, such as those of the free radical type to produce homopolymers, copolymers, terpolymers, etc.

The ethylenically unsaturated monomers that can be emulsion copolymerized with TMI derived monomers contain at least one nonaromatic double bond. These ethylenically unsaturated monomers are generally diene monomers or vinyl monomers. The ethylenically unsaturated monomers generally contain from 2 to 16 carbon atoms. Some representative examples of ethylenically unsaturated monomers that can be utilized in the emulsion polymerizations include diene monomers such as butadiene, isoprene, piperylene, chloroprene, and the like; alkyl acrylates, such as methyl acrylate, ethyl acrylate, butyl acrylate, methyl methacrylate, and the like; vinyl aromatics such as styrene, α-methylstyrene, bromostyrene, chlorostyrene, fluorostyrene, vinylanisole, and the like; vinyl halides, such as vinylbromide, chloroethene (vinyl chloride), 1,1-dichloroethylene (vinylidene chloride), and the like; vinyl esters such as vinyl acetate; α,β-olefinically unsaturated nitriles, such as acrylonitrile and methacrylonitrile; α,β-olefinically unsaturated amides, such as acrylamide, N-methyl acrylamide, N-t-butyl acrylamide, N-cyclohexyl acrylamide, diacetone acrylamide, methacrylamide, N-ethyl methacrylamide, and the like; vinyl pyridine; methacrylates, such as n-octyl methacrylate and dodecyl methacrylate; hydroxyethylacrylate; polyfunctional compounds such as ethylene glycol dimethacrylate, diethylene glycol diacrylate, divinyl benzene, alkenyl pentaerythritol, methylene-bis-acrylamide, and the like.

In the polymerization of TMI derived monomers with one or more of the above-mentioned ethylenically unsaturated monomers there can be competing or side reactions which take place. Therefore, the choice of reactants, process conditions, the order of addition of reactants and the like should be selected in order to produce a useful polymer containing chain linkages (repeat units) which are derived from TMI derived monomers.

The emulsifiers or soaps used in the emulsion copolymerizations may be charged at the outset of the polymerization or may be added incrementally or by proportioning as the reaction proceeds. Generally, anionic emulsifier systems provide good results; however, any of the general types of anionic, cationic or nonionic emulsifiers may be employed in the polymerization.

Among the anionic emulsifiers that can be employed in the emulsion copolymerizations are fatty acids and their alkali metal soaps such as caprylic acid, capric acid, pelargonic acid, lauric acid, undecyclic acid, myristic acid, palmitic acid, margarmic acid, stearic acid, arachidic acid, and the like; amine soaps of fatty acids such as those formed from ammonia, mono-and dialkyl amines, substituted hydrazines, guanidine, and various low molecular weight diamines; chain-substituted derivatives of fatty acids such as those having alkyl substituents; napthenic acids and their soaps and the like; sulfuric esters and their salts, such as the tallow alcohol sulfates, coconut alcohol sulfates, fatty alcohol sulfates, such as oleyl sulfate, sodium lauryl sulfate and the like; sterol sulfates; sulfates of alkylcyclohexanols, sulfation products of lower polymers of ethylene as $C_{10}$ to $C_{20}$ straight chain olefins, and other hydrocarbon mixtures, sulfuric esters of aliphatic and aromatic alcohols having intermediate linkages, such as ether, ester, or amide groups such as alkylbenzyl (polyethyleneoxy) alcohols, the sodium salt of tridecyl ether sulfate, alkane sulfonates, esters and salts, such as alkylsulfonic acids with the general formula $RSO_2$—OH, wherein R is an alkyl group having from 1 to 20 carbon atoms; sulfonates with intermediate linkages such as ester and ether-linked sulfonates such as those having the formula $RCOOC_2H_4SO_3H$ and $RCOH_2$—$CH_2$—$SO_3H$, wherein R is an alkyl group having from 1 to 20 carbon atoms such as dialkyl sulfosuccinates; ester salts with the general formula:

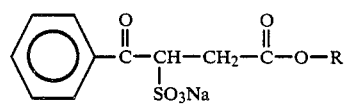

wherein R is an alkyl group having from 1 to 20 carbon atoms; aralkyl sulfonates in which the alkyl groups contain preferably from 10 to 20 carbon atoms, e.g. dodecylbenzenesulfonates, such as sodium dodecylbenzenesulfonate; alkyl phenol sulfonates; sulfonic acids and their salts such as acids with the formula $RSO_3Na$, wherein R is an alkyl and the like; sulfonamides, sulfamido methylenesulfonic acids; rosin acids and their soaps;

sulfonated derivatives of rosin and rosin oil; and lignin sulfonates, and the like. Of rosin acids, about 90 percent are isomeric with abietic acid and the other 10 percent is a mixture of dehydroabietic acid.

The emulsion copolymerizations are initiated with free radical initiator systems. Normally, the polymerization is initiated by the addition of such a free radical initiator system to a mixture of TMI derived monomers, the additional ethylenically unsaturated monomers, the emulsifier, and water which forms an aqueous reaction medium.

Some representative examples of free radical initiators which are commonly used include the various peroxygen compounds such as potassium persulfate, ammonium persulfate, dicetyl peroxydicarbonate, the various azo compounds such as 2-t-butylazo-2-cyanopropane, dimethyl azodiisobutyrate, azodiisobutyronitrile, 2-t-butylazo-1-cyanocyclohexane, 1-t-amylazo-1-cyanocyclohexane, and the like.

Numerous redox initiator systems can also be employed as the free radical initiator in order to initiate the emulsion copolymerization of TMI derived monomers with ethylenically unsaturated monomers. For example, such polymerizations can be initiated by utilizing ferrous/hydroperoxide redox initiators, metal persulfate/sodium metabisulfite redox initiators, $Cu^{2+}$/peroxydiphosphate redox initiators. $KMnO_4$/glucose redox initiators, and $Cu^{3+}$/hydroperoxide redox initiators. Potassium persulfate and ammonium persulfate can be used with great success as redox initiators when used in conjunction with sodium metabisulfite. Various metal persulfates (for example sodium and potassium) and ammonium persulfate (hereinafter the term metal persulfates will be meant to include ammonium persulfate) can be employed as redox initiators when used in conjunction with sodium metabisulfite, sodium thiosulfate, and sodium dithionite. Ferrous/hydroperoxide redox initiator systems are comprised of a ferrous compound which contains a divalent iron atom ($Fe^{2+}$) and a hydroperoxide compound which contains a —OOH group. Some representative examples of ferrous compounds that can be used in the redox initiator systems of this invention include ferrous ammonium gluconate, ferrous bromide, ferrous carbonate, ferrous chloride, ferrous fluoride, ferrous fluorosilicate, ferrous hyposulfite, ferrous iodide, ferrous nitrate, ferrous oxalate, ferrous perchlorate, ferrous sulfate, ferrous tartrate, and ferrous thiocyanate. Some representative examples of hydroperoxide compounds that can be utilized include 2,3-dimethylbutane hydroperoxide, methylcyclohexane hydroperoxide, cumene hydroperoxide, 2,2,5-trimethylhexane hydroperoxide, 1,2,3,4-tetrahydronaphthalene hydroperoxide, sec-butylbenzene hydroperoxide, p-cymene hydroperoxide, aliphatic alkylate hydroperoxide, 1-methyl-1,2,3,4-tetrahydronaphthalene hydroperoxide, 5-phenylpentene-2-hydroperoxide, chloroisopropylbenzene hydroperoxide, cyclohexylbenzene hydroperoxide, diisopropylbenzene hydroperoxide, isopropyl-1,3,3,4-tetrahydronaphthalene hydroperoxide, t-butylisopropylbenzene hydroperoxide, diisopropyltoluene hydroperoxide, 1,2,3,4,4a,9,20,10a-octahydrophenanthrene hydroperoxide, 5-(4-isopropylphenyl)-2-pentene hydroperoxide, (1-methylbutyl)-isopropylbenzene hydroperoxide, chlorodiisopropylbenzene hydroperoxide, triisopropylbenzene hydroperoxide, 1,2-diphenylbutane hydroperoxide, di-t-butylisopropylbenzene hydroperoxide, (1-methylhendecyl)-toluene hydroperoxide, 1,2-bis-(dimethylphenyl)-butane hydroperoxide, and (1-methylhendecyl)-isopropylbenzene hydroperoxide. The most preferred hydroperoxide compounds are 2,3-dimethylbutane hydroperoxide, cumene hydroperoxide, sec-butylene hydroperoxide, p-cymene hydroperoxide, and paramenthane hydroperoxide.

These redox initiator components can be employed at levels from about 0.0001 weight percent to about 0.05 weight percent based upon the total weight of the aqueous reaction medium. It is generally preferred for the initiator components to be employed at levels from about 0.0005 weight percent to 0.01 weight percent based upon the total weight of the aqueous reaction medium. The most preferred level for the initiator components is from 0.001 weight percent to 0.005 weight percent based upon the total aqueous reaction medium.

The temperature range over which the polymerizations can be conducted is from about $-20°$ C. to about $100°$ C. The preferred temperature range is from $-5°$ C. to $80°$ C. with the most preferred temperature being from $5°$ C. to $60°$ C. The reaction time allowed for the polymerization to occur (time period between the initiation of the polymerization and its termination) is generally in the range of about 0.5 to 50 hours. However, in most cases a reaction time of 4 to 16 hours can be employed. This reaction time will vary with the temperature at which the polymerization is conducted, with the type of redox initiator system employed, and with the level of initiator used.

It is sometimes desirable to use deionized water in the preparation of the aqueous reaction medium used in the polymerization of this invention. For best results oxygen which is dissolved in the water and monomers should be removed before polymerization. This can be accomplished by sparging the monomers and water used in the reaction medium with an inert gas or nitrogen.

The aqueous reaction medium will normally contain from about 40 weight percent to about 95 weight percent water, from about 5 weight percent to about 60 weight percent monomers (including TMI derived monomers), and from about 0.1 weight percent to about 10 weight percent emulsifiers, based upon the total weight of the aqueous reaction medium. Preferably, the aqueous reaction medium will contain 50 to 90 weight percent water, 10 to 50 weight percent monomers, and 0.3 to 5 weight percent soaps. More preferably, the aqueous reaction medium will contain 60 to 80 weight percent water, 20 to 40 weight percent monomers, and 0.5 to 2 weight percent emulsifiers.

The monomer component of the aqueous reaction medium will normally contain from about 0.1 to about 50 weight percent TMI derived monomers and from about 50 weight percent to about 99.5 weight percent ethylenically unsaturated monomers. Preferably, the monomer component of the aqueous reaction medium will be comprised of from 1 to 30 weight percent TMI derived monomers and from 70 to 99 weight percent ethylenically unsaturated monomers.

The polymerization of TMI derived monomers into polymers results in the polymer formed containing segmers having the structural formula:

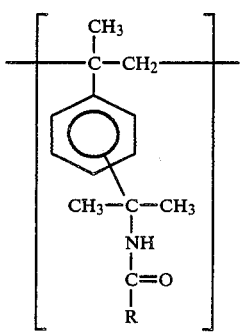

wherein R represents a moiety that contained an active hydrogen atom.

The following examples illustrate the different types of TMI derived monomers that the instant invention is concerned with.

EXPERIMENTAL 1

Preparation of 2-[3-(butylthio)-2-methyl-propionyloxy]ethyl N[α,α'-dimethyl-3-isopropionylbenzyl]carbamate To a reaction bottle was added 19.4 g of 2-[3-(n-butyl-thio)-2-methylpropionyloxy]ethylmethacrylate, 21 g m-TMI, 41 g of toluene, 3 drops of triethylamine and 0.10 g of dibutyltindilaruate. The bottle was put on a bottle roller at room temperature for 72 hours. The solvent was removed to give the desired product.

EXPERIMENTAL 2

Preparation of:

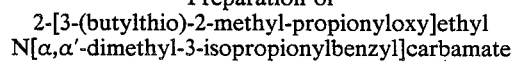

To a bottle was added 17 g of 2,2'methylene-bis(4-methyl-6-t-butylphenol), 10.3 g of m-TMI, 50 g of toluene, 20 drops triethylamine and 2.0 drops of dibutyltindilaruate. The reaction bottle was put in a 70° oven and allowed to react without mixing for 18 hours. TLC then confirmed that a product had formed. The solvent was distilled off and the product washed with hexane. The melting point was 135°–136° C.

EXPERIMENTAL 3

Preparation of:

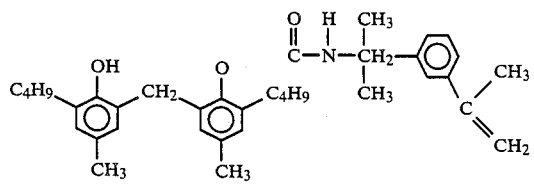

To a reaction bottle was added 30 grams of N-phenyl-N'-isopropyl-p-phenylenediamine, 26.6 grams of m-TMI, 40 grams toluene, 20 grams tetrahydrofuran and 3 drops of dibutyltindilaruate. The reaction bottle was put on a bottle roller at room temperature for 16 hours. The solvent was removed and the product washed with hexane. The melting point was 128°–129° C.

EXPERIMENTAL 4

Preparation of:

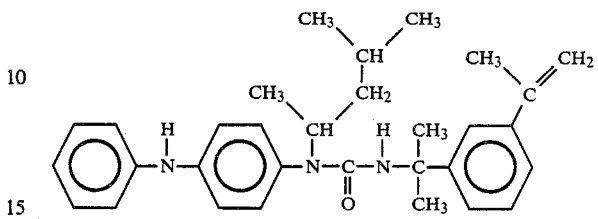

The procedure of Experimental 3 was used except the amine was N-phenyl-N'-(1,3 dimethylbutyl)-p-phenylenediamine.

EXPERIMENTAL 5

Preparation of:

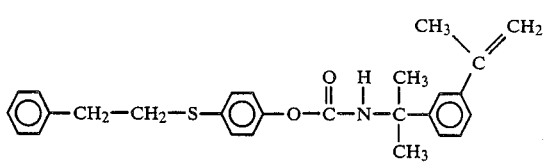

To a bottle was added 20.5 g of m-TMI, 23.1 g of 4-phenylethylthiophenol, 20 g of toluene, 2 drops of dibutyltindilaruate and 3 drops of triethylamine. The reaction was again conducted on a bottle roller at room temperature. Formation of the product was indicated by NMR. Melting point was 81°–83° C.

EXPERIMENTAL 6

Preparation of:

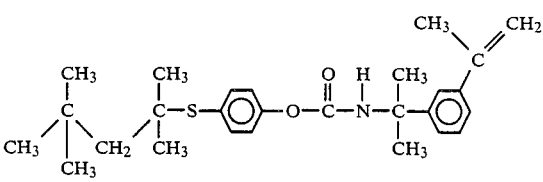

To a reaction bottle was added 8 g of 4-(1,1,3,3-tetramethylbutylthio) phenol, 7 g of m-TMI, 30 g of toluene, 5 drops of triethylamine and 2 drops of dibutyltindilaruate. After reacting at 64° C., the solvent was removed. The product crystallized from hexane. The melting point was 88°–89° C.

EXPERIMENTAL 7

Preparation of:

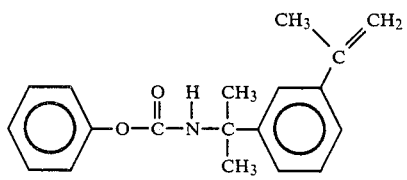

To a bottle was added 9.4 g of phenol, 20.2 g of m-TMI and 1 drop of dibutyltindilaruate. The bottle was placed in a 65° C. oven and allowed to stand for 4½ hours. The product solidified when cooled to room temperature and was recrystallized from a mixture of THF, toluene and hexane. The white powder had a melting point of 103.5°–106° C.

EXPERIMENTAL 8

Preparation of an amine terminated polyethylene/propylene oxide copolymer adduct with m-TMI To a bottle was added 20 g of Jeffamine-600 (TM of Texaco), 6.7 g of meta-TMI and 30 g of toluene. The reactor immediately warmed while shaking by hand. It was cooled and then put on a bottle roller. Stripped to remove the solvent.

EXPERIMENTAL 9

Preparation of:

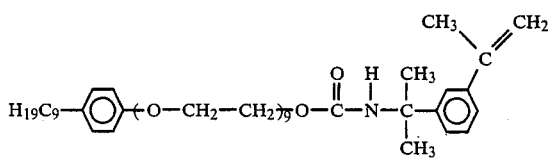

To a bottle was added 33 g of Igepal™ CO-630 from GAF Corporation, 10 g of m-TMI, 3 drops of dibutyltindilaruate and 3 drops of triethylamine. The reactor was placed in a 65° C. oven for 18 hours. Formation of the product was indicated by TLC and NMR.

EXPERIMENTAL 10

Preparation of:

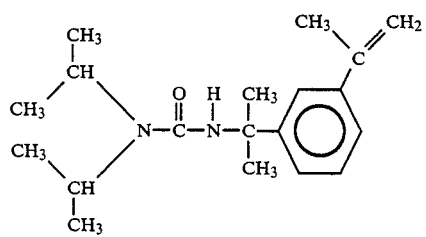

To a bottle was added 10 g of meta-TMI, 10 g of toluene, 9 g of THF and 5.5 g of diisopropylamine. There was an immediate exothermic reaction. It was cooled and then put on a bottle roller. The product was washed with water and then the solvent stripped off. A white crystalline product was isolated.

EXPERIMENTAL 11

Preparation of:

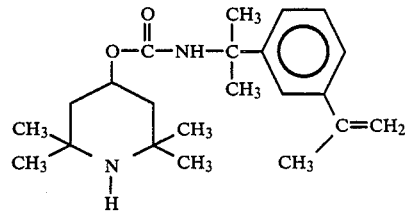

Into an erylenmeyer flask equipped with a magnetic stirrer was placed 15 g of m-TMI (75 mmole) and 10 g (64 mmol) of 2,2,6,6-tetramethyl-4-piperdinol, 50 cc of toluene and 2 drops of dibutyl tin dilaurate (catalyst). The mixture was heated to dissolve all reactants and allowed to stand overnight. A precipitate formed and was filtered to yield 9.0 g of product. The solvent was removed from the filtrate to leave an oil which crystallized on standing. Recrystallization from 80 cc of hexane provided 11.0 g of the product. Total yield was 87%, 20.0 g.

The product is a polymerizable U.V. stabilizer or HALS (hindered amine light stabilizer). Polymeric HALS have been prepared, see U.S. Pat. No. 4,435,555; however, there is no disclosure or suggestion of placing an olefin functionality on a HALS.

EXPERIMENTAL 12

Preparation of:

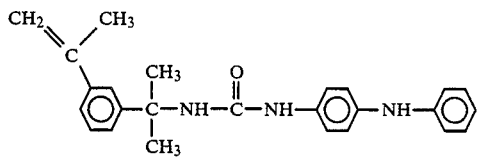

N'-[1-(3-isopropenylphenyl)-1-methyl]ethyl-N-3-[4-(phenylamine)phenyl]urea

To a 500 ml three neck flask was charged 18.4 g (0.1 mole) p-aminodiphenylamine, 20.1 g (0.1 mole) m-TMI and 100 ml toluene. A condenser was attached and the mixture was heated at reflux for three hours. Upon cooling, the product separated. 300 ml of hexane was then added and the mixture was stirred and filtered. The filtercake was washed with hexane and dried to yield 36.0 g of product (93.5% crude yield). The crude product was purified by dissolving in 300 ml of warm methanol and treating with 10.0 g Filtrol 13LM bleaching clay. The clay was filtered off and the filtrate was added to cold water to precipitate the product as a white powder. Melting point 149°–152° C.

EXPERIMENTAL 13

Preparation of:

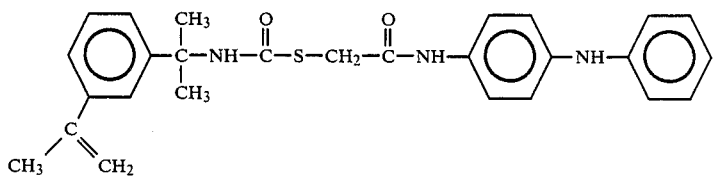

4-(phenylamino)phenyl carbamoylmethyl-N-[1-(3-isopropenylphenyl-1-methyl-]ethyl thiocarbamate To a 500 ml three neck flask was charged 25.8 g (0.10 mole) of N-(4-anilinophenyl)-mercaptoacetamide (MADA), 20.1 g (0.10 mole) of m-TMI and 200 ml of xylene. The mixture was heated at reflux for 18 hours. The solvent was striped off to obtain a viscous brown oil. IR Analysis of the oil indicated no isocyanate absorption but a strong NH stretch at 3300 cm$^{-1}$ and carbonyl band at 1650 cm$^{-1}$.

EXPERIMENTAL 14

Preparation of:

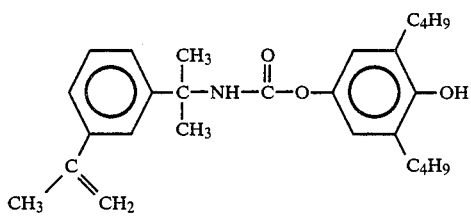

3,5-di-t-butyl-4-hydroxyphenyl-N-[1-(3-isopropenylphenyl)-1-methyl]ethyl carbamate To a 250 ml three neck flask was charged 10.05 g (0.05 mole) of m-TMI, 11.1 g (0.05 mole) 2,6-di-t-butyl hydroquinone and 75 ml xylene. The mixture was heated at reflux under nitrogen for 2 hours, then 1 g tin octanoate catalyst was added. The mixture was refluxed for 2 additional hours. The reaction mixture was cooled and the solvent was stripped at reduced pressure. Over a period of one week, the viscous product crystallized. The product was recrystallized for hexane to obtain 16.0 g (76% yield) of a white crystalline material. Melting point was 110°–114° C. IR and NMR analysis indicated the desired product.

EXPERIMENTAL 15

Polymerization of Functionalized TMI Monomer

The monomer prepared in Experimental 1 was copolymerized at the 10 part level (with 66 parts butadiene and 24 parts acrylonitrile) in an NBR recipe. The polymer latex was coagulated in isopropyl alcohol and then extracted with hot methanol for 36 hours. The polymer sulfur content (after subtracting out the contribution of the chain transfer agent) was found to be 0.496%. Hence 6.5 parts of the monomer prepared in Experimental 1 copolymerized into the NBR polymer.

EXPERIMENTAL 16

The monomer prepared in Experimental 1 was copolymerized in a standard cold SBR recipe. The monomer was copolymerized at the 10.2 part level with 26.7 parts of styrene and 63.1 parts of butadiene. The resulting polymer was found to contain 7.8 parts of the monomer prepared in Experimental 1.

EXPERIMENTAL 17

The procedure was the same as Experimental 16 except the monomer prepared in Experimental 3 was copolymerized in the NBR recipe at the 3.16 part level. The polymer was coagulated and then extracted continuously with hot methanol.

EXPERIMENTAL 18

The monomer prepared in Experimental 11 was copolymerized into a styrene-butadiene resin.

EXPERIMENTAL 19

The extracted polymer prepared in Experimental 17 which contained the monomer prepared in Experimental 3 was evaluated in an oxygen adsorption test. This testing procedure is described in detail in Industrial and Engineering Chemistry, 43, p. 456 (1951) and Industrial and Engineering Chemistry, 45, p. 392 (1953). As a control, a similar polymer was prepared except that 1.76 parts of the polymerizable antidegradant

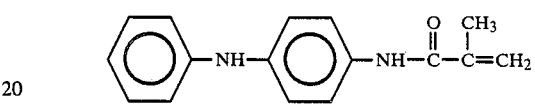

was charged to the polymerization reaction instead of the compound prepared in Experimental 3. This control polymer was also coagulated and extracted. The two polymers were evaluated by the oxygen absorption test at 100° C. The control polymer absorbed 1.09% by weight O$_2$ after 315 hours while the experimental polymer required 505 hours to reach the same level of oxygen absorption.

EXPERIMENTAL 20

Polymers prepared in a manner similar to Experimental 18 which contained the HALS/TMI monomer were evaluated for U.V. resistance. The tetramethyl piperidine/TMI adduct was incorporated in the polymerization charge at 1 and 3 part levels. Two controls were prepared. One contained 0.5 pphr Tinuvin P (a substituted hydroxyphenyl benzotriazole), a commercial U.V. stabilizer from Ciba-Geigy.

The experimental samples were dissolved in xylene at 33⅓% solids. The solution was used to cast films on aluminum panels to give 1 mil thickness on drying. Panels were dried 24 hours prior to testing. The panels were exposed on a turntable under a U.V. lamp for 536 hours.

The tristimulus "b" color (− blue, + yellow) is measured before and after testing to determine the color change (more yellow) due to exposure. The "b" represents the color change. The lower the number the better the U.V. resistance. The data presented in Table I represents the average of duplicate panels.

TABLE I

| | Panel | Initial | "b" Color After 536 hrs. | "b" |
|---|---|---|---|---|
| 1 | 1.0 pphr tetramethyl piperidine/TMI | −2.1 | 9.1 | 11.2 |
| 2 | 3.0 pphr tetramethyl piperidine/TMI | −2.1 | 6.3 | 8.4 |
| 3 | Control- No Stabilizer | −1.9 | 8.3 | 10.2 |
| 4 | Control- 0.5 pphr Tinuvin P | −2.0 | 6.8 | 8.8 |

From the table it is evident that Panel 2 had the best U.V. resistance.

Industrial Applicability

This invention provides novel compositions of matter that are polymerizable antidegradant monomers. As demonstrated, m- or p-TMI can be reacted with various rubber chemicals, e.g. antioxidants, antiozonants, synergists, plasticizers, cure activators, accelerators, retarders, etc., to yield functionalized monomers that, when polymerized, form polymers having pendant to the polymeric backbone the desired rubber chemical functionality.

In contrast to conventional synthetic methods for producing polymerizable antidegradants which involve multi-step processes, the reaction of TMI with active hydrogen compounds proceed cleanly and in high yields, thus decreasing costs.

The foregoing detailed description has been given for clearness of understanding only, and no unnecessary limitations are to be understood therefrom. Obvious modifications of this invention will occur to those skilled in the art.

The embodiments of the invention in which an exclusive property or privilege is claimed are defined as follows.

We claim:

1. A compound selected from the group consisting of:

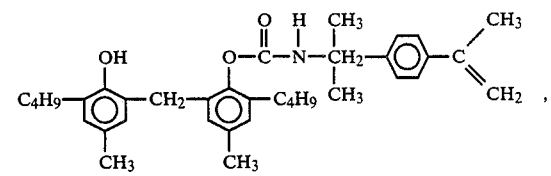

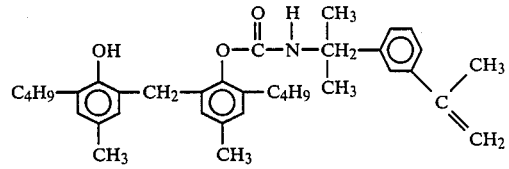

2. The compound of claim 1 wherein said compound is:

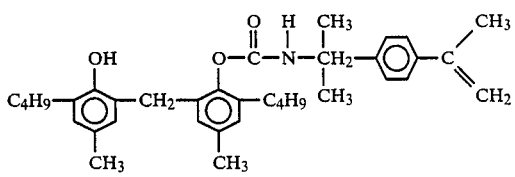

3. The compound of claim 1 wherein said compound is:

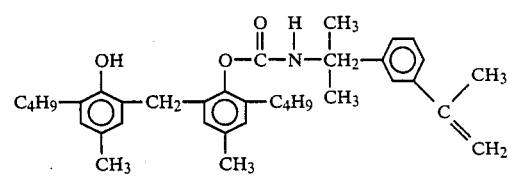

* * * * *